United States Patent [19]
Archibald et al.

[11] Patent Number: 5,642,733
[45] Date of Patent: Jul. 1, 1997

[54] BLOOD PRESSURE SENSOR LOCATOR

[75] Inventors: G. Kent Archibald, Vadnais Heights; Orland H. Danielson, Roseville; Roger J. Woessner, St. Paul, all of Minn.

[73] Assignee: Medwave, Inc., St. Paul, Minn.

[21] Appl. No.: 628,082

[22] Filed: Apr. 8, 1996

[51] Int. Cl.⁶ ............................................. A61B 5/02
[52] U.S. Cl. ........................... 128/672; 128/668; 128/687
[58] Field of Search .................................. 128/633, 664–8, 128/672, 677, 678, 687, 689–691, 696; 604/115, 116

[56] References Cited

U.S. PATENT DOCUMENTS

| | | | |
|---|---|---|---|
| 4,993,422 | 2/1991 | Hon et al. | 128/672 |
| 5,025,792 | 6/1991 | Hon et al. | 128/672 |
| 5,195,522 | 3/1993 | Pytel et al. | 128/690 |
| 5,243,992 | 9/1993 | Eckerle et al. | 128/690 |
| 5,271,405 | 12/1993 | Boyer et al. | 128/672 |
| 5,406,952 | 4/1995 | Barnes et al. | 128/672 |

*Primary Examiner*—Lee S. Cohen
*Assistant Examiner*—Bryan K. Yarnell
*Attorney, Agent, or Firm*—Kinney & Lange, P.A.

[57] ABSTRACT

A blood pressure sensor locator for locating a blood pressure sensing device over an underlying artery of a patient includes a base, an adhesive on an underside of the base for coupling the base to an anatomy of the patient and a guide supported by the base and configured for contacting the sensing device to locate an aligned sensing device over the underlying artery.

25 Claims, 3 Drawing Sheets

5,642,733

BLOOD PRESSURE SENSOR LOCATOR

BACKGROUND OF THE INVENTION

The present invention relates to systems for measuring blood pressure. In particular, the invention relates to a method and apparatus for indicating and maintaining a blood pressure sensing device over an underlying artery.

Blood pressure may be measured either invasively or non-invasively. Invasively measuring blood pressure using an arterial line (A-LINE) involves insertion of a needle into the artery. A transducer connected to the needle by a fluid column is used to determine exact arterial pressure from the inserted needle.

Alternatively, blood pressure may be measured non-invasively. Non-invasive measurement of blood pressure typically requires that an external blood pressure sensing device having a sensing surface be positioned over and above an artery. Typically, a physician will palpate the artery and mark a location above the artery. The sensing surface of the sensing device is then centered over this mark.

Although seemingly simple, accurately locating the external blood pressure sensing device over the underlying artery may be extremely difficult. Because the sensing device is often opaque and has a surface area much larger than the mark indicating the location of the artery, a physician cannot view the mark or the underlying artery while positioning the sensing device. As a result, centering the sensing device over the mark or over the underlying artery is extremely difficult and time consuming.

This problem is further magnified because the sensing device is frequently removed or becomes dislodged from its original location and must be repeatably repositioned over the artery. For example, during a typical hospital procedure, the patient may be moved from pre-operative care to surgery, to recovery, to intensive care and then to a less acute care step down area of the hospital. At each location, a physician must relocate and once again center the sensing device over the mark indicating the underlying artery. In instances where the mark has worn away, the physician must once again palpate the artery, mark the location and center the sensor over the mark. As a result, the necessity of repeatedly centering the sensor over the mark or identifying the location of the artery is time consuming and expensive.

Once the sensor is centered over the mark and above the underlined artery, patient movement frequently moves and dislodges the sensor from its original position. Consequently, the sensor must once again be recentered over the mark and above the underlying artery. Although accidental movement of the sensor from its original location may be minimized by the physician tightening a strap or other structure that holds the sensing device about the wrist, tightening of the strap or belt may cut off or reduce blood flow. This reduction of blood flow may cause swelling of the patient's hand or other related anatomy.

SUMMARY OF THE INVENTION

The present invention is a blood pressure sensor locator for locating a blood pressure sensing device over an underlying artery of a patient. The locator of the present invention includes a base, means for coupling the base in a selected position adjacent an anatomy of the patient proximate the underlying artery and a guide supported by the base and configured for contacting the sensing device to locate and align the sensing device over the underlying artery.

In a preferred embodiment, the base is flexible so as to conform to the anatomy of the patient and at least partially defines openings that extend through the base. The openings are configured for at least partially receiving the sensing device so that the base at least partially mates with the sensing device to guide positioning of the sensing device relative to the locator and relative to the underlying artery. The base is preferably coupled in a selected position adjacent the anatomy of the patient proximate the underlying artery by an adhesive on an underside of the base.

As a further refinement to the blood pressure sensor locator of the present invention, a transparent thin film spans the opening and includes alignment marks for aligning the opening and the locator over the underlying artery. For further assistance in aligning the locator or the underlying artery, the base includes alignment marks as well. To ensure proper alignment of the sensing device with respect to the locator and to assist in maintaining the blood pressure sensing device in its position relative to the locator and to the underlying artery, the base further defines at least one additional opening for at least partially receiving a portion of the sensing device.

DETAILED DESCRIPTION OF THE PREFERRED EMBODIMENTS

Figure 1:
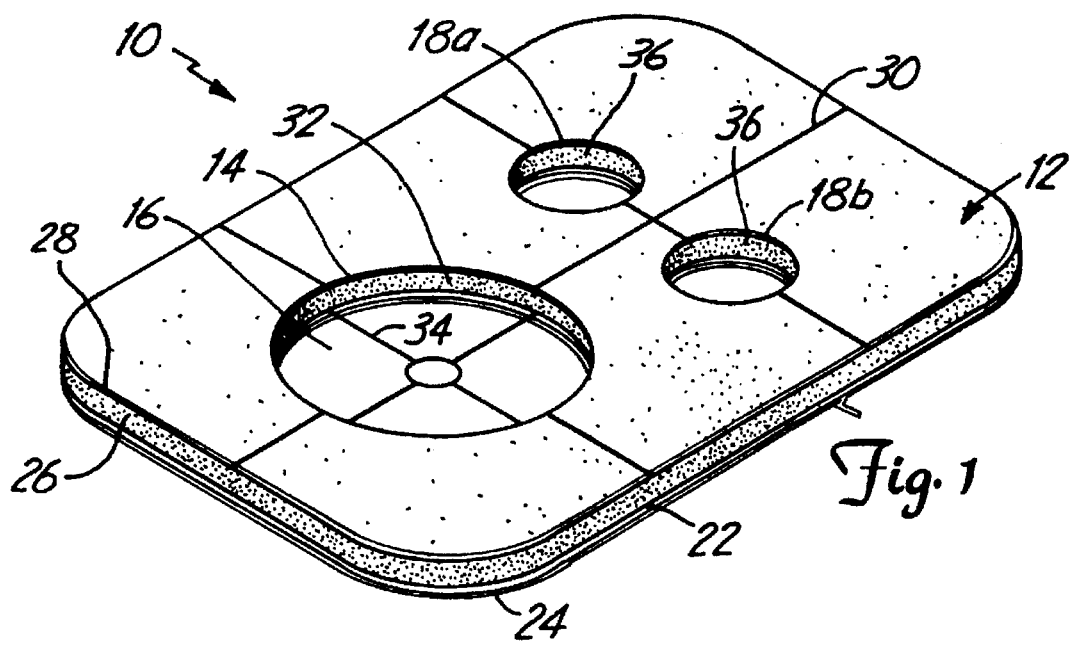
FIG. 1 is a perspective view of a blood pressure sensor locator of the present invention.
Figure 2:
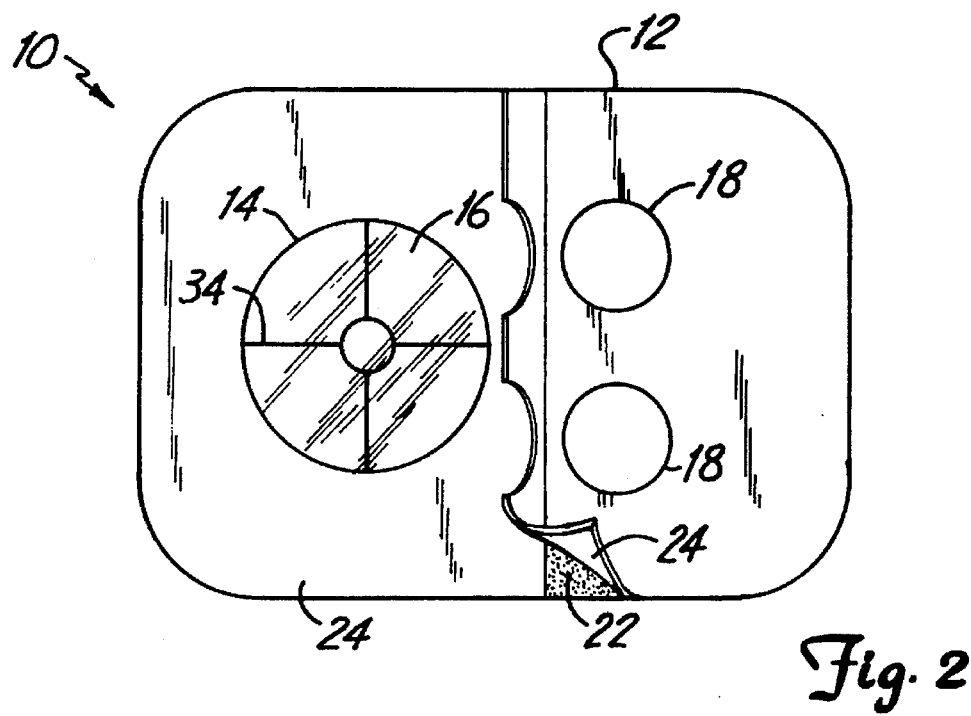
FIG. 2 is a bottom plan view of the sensor locator.

FIGS. 1 and 2 illustrate blood of pressure sensor locator 10. FIG. 1 is a perspective view of sensor locator 10. FIG. 2 is a bottom elevational view illustrating an underside of sensor locator 10. As best shown by FIG. 1, blood pressure sensor locator 10 is preferably a generally flat template or pad and includes base 12, artery locating window 14, transparent film 16, sensor support locating windows 18a, 18b, adhesive layer 22 and removable backing 24. Base 12 is a generally flat sheet defining windows 14 and 18a, 18b. Base 12 is preferably formed from two layers 26 and 28 that are fixedly coupled to one another by adhesive or glue. Layer 26 is soft and flexible, and provides base 12 with a desired thickness. Layer 26 preferably has a thickness of about 3/32 of an inch. Layer 26 is preferably formed from an open cell, breathable polyurethane foam.

Layer 28 is a liner preferably formed from a breathable medical grade material less stretchable than the material forming layer 26. Preferably, layer 28 is a perforated membrane of a foil or plastic. Layer 28 acts as a spine by providing dimensional stability to base 12 while also providing base 12 with the necessary flexibility for permitting base 12 to comfortably wrap about a patient's anatomy. Layer 28 is preferably formed from a medical grade film such as breathable polyurethane and preferably has a thickness of about 0.001 inches. Because layers 26 and 28 of base 12 are formed from lightweight, breathable and flexible material, base 12 is easily adaptable so as to wrap about varying anatomies and is lightweight for patient comfort. As can be appreciated, base 12 may alternatively be formed from a multitude of materials or a single layer of a material.

To aid in centering sensor locator 10 and window 14 over and around an underlying artery, base 12 additionally includes alignment marks 30. Alignment marks 30 extend along an upper surface of base 12 and are preferably in the form of intersecting cross hairs that intersect one another at a center of window 16. Alternatively, alignment marks 30 may constitute any one of a variety of alignment indicators such as protrusions, indentations or edges formed as part of base 12. Alignment marks 30 enable a physician to center and align a location corresponding to the underlying artery with a selected portion of locator 10 to ensure that window 18 is centered around and above the underlying artery.

Figure 3:
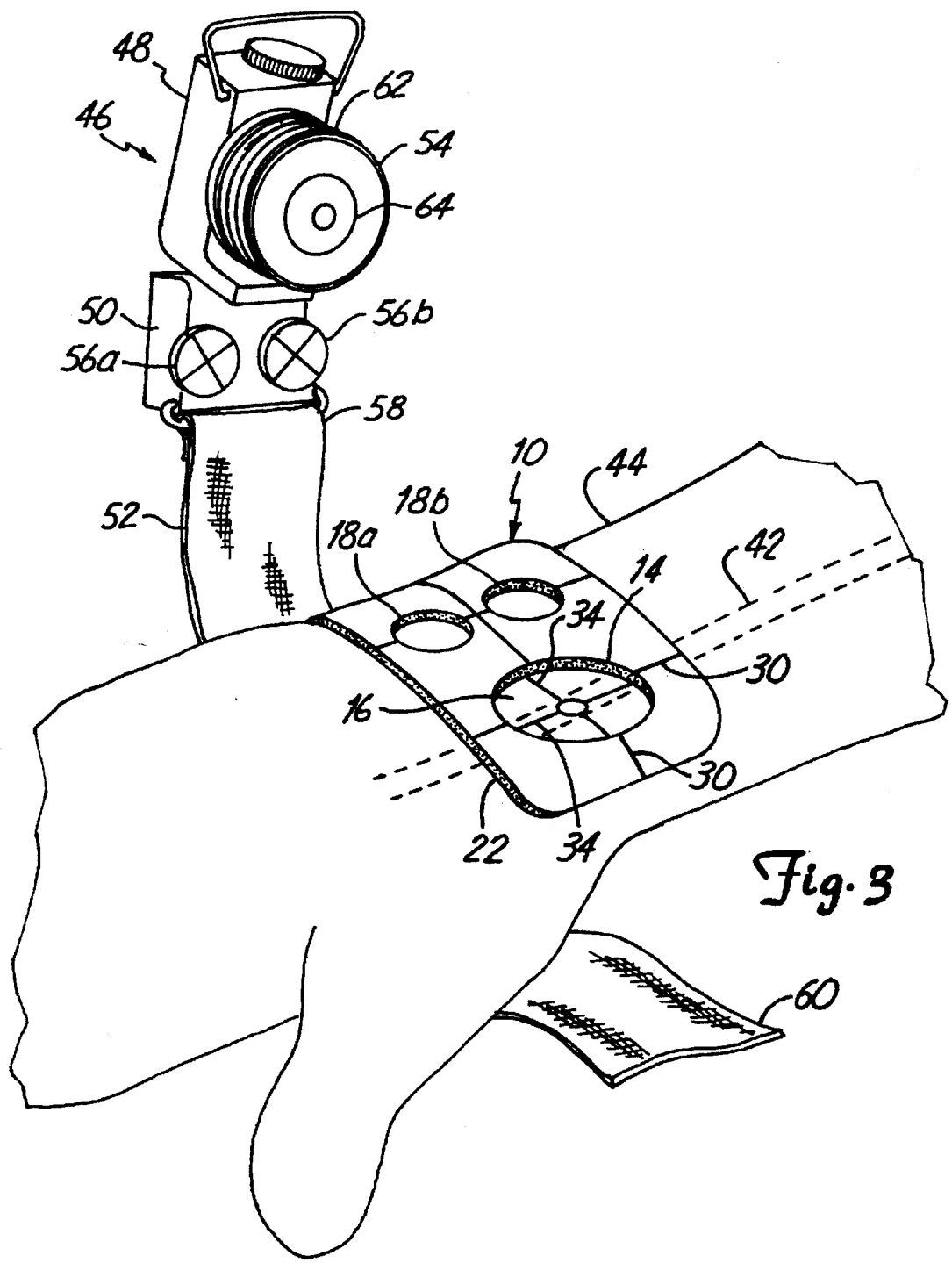
FIG. 3 is a perspective view of the sensor locator mounted upon a wrist and a blood pressure sensing device spaced above the sensor locator.

Artery locating window 14 comprises an opening extending completely through base 12. Window 14 enables a physician to locate sensor locator 10 over the underlying artery without obstructing the view of the underlying artery or a mark indicating the position of the underlying artery. Window 14 is preferably sized greater than or equal to the size and dimension of an anatomy engaging sensing member of an external blood pressure sensing device such as sensor interface 54 of sensing device 46 shown in FIG. 3. Preferably, window 14 is sized and shaped so as to correspond with a size and shape of the anatomy engaging member. For example, sensor interface 54 illustrated in FIG. 3 is circular. Accordingly, window 14 is also circular and has a diameter slightly larger than a diameter of sensor interface 54 to enable window 14 to receive sensor interface 54. Due to the shape of window 14, surfaces 32 of base 12 that define window 14 abut and mate with sensor interface 54 to guide positioning of sensor interface 54 and sensing device 46.

Film 16 spans window 14 and is formed from a thin transparent material for enabling a physician to view the anatomy of a patient to view marks on the anatomy of the patient and to palpate the artery of the patient below film 16. Film 16 is preferably fixedly coupled to layer 22 of base 12. Film 16 preferably has a thickness of between about 0.001 inches to about 0.002 inches and is preferably formed from a medical grade film such as breathable polyurethane. To assist in centering sensor locator 12 and window 14 with respect to an underlying artery, film 16 includes alignment marks 34. Alignment marks 34 are preferably in the form of cross hairs that intersect one another at a common point or location. Alignment marks 34 enable a physician to precisely and accurately position and center window 14 over and around the underlying artery.

As can be appreciated, alignment marks 34 may comprise any one of a variety of alignment indicators or markings such as a single circle or point at the center of window 14 or arrows pointing to a center of window 14. As can further be appreciated, depending upon the shape and configuration of sensor interface 38, it may be desirable to alternatively position the underlying artery at a location other than a concentric center of window 14 for measuring blood pressure. In such an alternative arrangement, alignment marks 30 and 34 are positioned to indicate to a physician the alternative preferred positioning of the underlying artery with respect to window 14. As can further be appreciated, because alignment marks 30 may be independently used to position window 14 with respect to the underlying artery, film 16 and alignment marks 34 may be omitted entirely.

Windows 18a, 18b comprise openings that extend through base 12 and are spaced from window 14 for at least partially receiving portions of a sensing device such as wrist pads 56a, 56b, respectively, of sensing device 46 shown in FIG. 3. Alternatively, windows 18a, 18b may extend only partially into base 12 so as to provide impressions or detents for at least partially receiving portions of a sensing device. Windows 18 are preferably spaced from window 14 and positioned with respect to window 14 so as to correspond to the positioning of the anatomy engaging sensing member and the other portions of the sensing device. Windows 18a, 18b align the sensing device relative to sensor locator 10 to ensure that the sensing device is accurately positioned with respect to sensor locator 10 and also with respect to the underlying artery. Because windows 18a, 18b are spaced from one another as well as window 14, windows 18a, 18b and window 14 provide three distinct and spaced apart guiding or alignment points to prevent the sensing device from being positioned in a backwards or incorrect orientation. Because windows 18a, 18b preferably have a shape and size different than the size and shape of window 14, windows 18a, 18b prevent the anatomy engaging sensing member such as sensor interface 54 shown in FIG. 3 from being incorrectly positioned relative to sensor locator 10. Because windows 18a, 18b are sized and shaped to at least partially correspond with the size and shape of portions of the sensing device, such as wrist pads 56a, 56b shown in FIG. 3, surfaces 36 of base 12 at least partially mate with and abut the portions of the sensing device to guide the positioning and alignment of the sensing device relative to sensor locator 10. Alternatively, other structures may be used to align the sensing device with sensor locator 10. For example, instead of using openings or detents for aligning the sensing device with sensor locator 10, sensor locator 10 may use protrusions or projecting members which mate with corresponding detents in the sensing device. In addition, sensor locator 10 may alternatively include alignment marks or other indicia for assisting a physician in the alignment of the sensing device with sensor locator 10. Furthermore, because base 12 has a non-deminimus thickness, preferably 3/32 of an inch, surfaces 36 also stabilize and maintain sensing device in place.

As best shown by FIG. 2, adhesive layer 22 and backing 24 extend along a lower surface of base 12. Backing 24 is illustrated as being partially pealed back away from base 12 and away from adhesive layer 22 to expose adhesive layer 22. Adhesive layer 22 is preferably coated across an entire lower surface of base 12. Alternatively, adhesive layer 22 may be selectively coated or applied to only selected areas of base 12 as desired. Furthermore, adhesive layer 22 may alternatively comprise adhesive film, tape or other adhesive means. Adhesive layer 22 is preferably a medical grade adhesive having an adhesiveness such that base 12 may be securely mounted or coupled to an anatomy of the patient proximate the underlying artery and yet removable from the anatomy of the patient when desired. Adhesive layer 22 maintains the positioning of sensor locator 10 relative to the anatomy of the patient and the underlying artery. As a result, base 12 and windows 14, and 18a, 18b of sensor locator 10 maintain their initial accurate positioning during patient movement and during movement of the patient between different hospital locations. Consequently, once accurately located above the underlying artery, sensor locator 10 enables a physician to quickly and easily identify the proper and accurate positioning of a sensor with respect to the underlying artery. In addition, sensor locator 10 also enables a physician to quickly and easily position the sensor at the accurate location without the need for palpating the artery or recentering the sensor with respect to the underlying artery. Furthermore, adhesive layer 22 also secures base 12 and sensor locator 10 to the anatomy of the patient without the need for straps, belts or other coupling devices encircling the entire anatomy which may cut-off or reduce blood flow. Alternatively, base 12 of sensor locator 10 may be secured in place relative to wrist 44 by other conventional mounting means such as a strap coupled to opposite ends of base 12 and encircling wrist 44.

Backing 24 covers adhesive layer 22 to prevent contamination of adhesive layer 22 and to prevent adhesive layer 22 from accidentally bonding to other objects. Prior to use of locator 10, backing 24 is peeled away from adhesive layer 22 to expose adhesive layer 22 on base 12. Adhesive layer 22 may then be positioned adjacent to the anatomy of the patient once the location of the underlying artery is identified.

In the preferred embodiment illustrated, base 12 preferably has a length of about 3.50 inches and a width of about 2.50 inches. Windows 18a, 18b preferably have a diameter of about 0.63 inches and have center points which are spaced from one another by about 0.90 inches. Each window 18a, 18b has a center point of approximately 0.8 inches from the sides of base 12 and 1.0 inches from a lower end of base 12. Window 14 preferably has a diameter of about 1.25 inches and has a center point preferably spaced from the lower end of base 12 by about 2.25 inches and spaced from the sides of base 12 by about 1.25 inches. The preferred dimensions of sensor locator 10 enables sensor locator 10 to comfortably wrap partially about a wrist of a patient and to stably secure a sensing device over an underlying artery.

FIG. 3 is a perspective view illustrating sensor locator 10 secured in place over an underlying artery 42 (shown in dashed lines) of a patient's wrist 44. FIG. 3 further illustrates a blood pressure sensing device 46 for sensing blood pressure of artery 42. Blood pressure sensing device 46 is substantially disclosed in U.S. patent application Ser. No. 08/388,752 entitled WRIST MOUNTED BLOOD PRESSURE SENSOR (herein incorporated by reference) and assigned to Medwave, Inc. Sensing device 46 generally includes holddown assembly 48, swivel mount 50, wrist mount 52, sensor interface 54 and wrist pads 56a, 56b. Holddown assembly 48 and swivel mount 50 are pivotally coupled to one another for conforming to wrist 44. Holddown assembly 48 supports sensor interface 54 while swivel mount 50 supports wrist pads 56a, 56b. Holddown pressure assembly 48 additionally applies force to sensor interface 54 and to artery 42. Sensor interface 54 preferably includes a side wall 62 and an active portion 64 for sensing blood pressure pulses of artery 42. Wrist pads 56a, 56b are configured for being positioned over and proximate to a surface of wrist 44. Wrist pads 56a, 56b support sensing device 46 adjacent to wrist 44. Wrist mount 52 has a first end 58 coupled to swivel mount 50 and a second end 60 which is configured for coupling to holddown assembly 48. Holddown assembly 48, swivel mount 50 and wrist mount 52 substantially encircle and wrap about wrist 44 to support sensor interface 54 over artery 42.

In use, sensor interface 54 is preferably positioned concentrically over artery 42 proximate a surface of wrist 44. Holddown assembly 48 preferably applies a varying pressure to sensor interface 54 and to the underlying artery 42. Holddown assembly 48 also regulates the tightness of wrist mount 52 about wrist 44 to prevent constriction of blood flow through wrist 44. Sensor interface 54 interfaces between artery 42 and a sensor (not shown) such as a transducer to calculate the blood pressure of artery 42 based upon signals produced by sensing device 46.

As best shown by FIG. 3, sensor locator 10 is adhesively secured to wrist 42 by adhesive layer 22. Sensor locator 10 is positioned about wrist 44 so as to locate window 14 and film 16 over the underlying artery 42. In particular, a physician must identify the location of artery 42. Generally, this is achieved by palpating artery 42. Once the physician identifies the location of artery 42, the physician preferably makes a mark on wrist 44 directly above the identified location of artery 42. It is this mark that the physician aligns with alignment marks 30 and 34 to accurately and precisely position sensor locator 10 on wrist 44 above artery 42. Because sensor interface 54 is generally circular and has a concentric center in communication with a transducer (not shown) for sensing blood pressure pulses, the center of window 14, as indicated by alignment marks 30 and alignment marks 34, is centered over artery 42. Once properly positioned, sensor locator 10 indicates the exact location at which sensing device 46 must be positioned so as to center and align sensor interface 54 over the underlying artery 42. During transportation of the patient, sensor locator 10 may be left in place. As a result, in lieu of reidentifying the location of underlying artery 42 and in lieu of recentering sensor interface 54 over artery 42, the physician may simply and easily position sensing device 46 over artery 42 by using window 14 of sensor locator 10.

Figure 4:
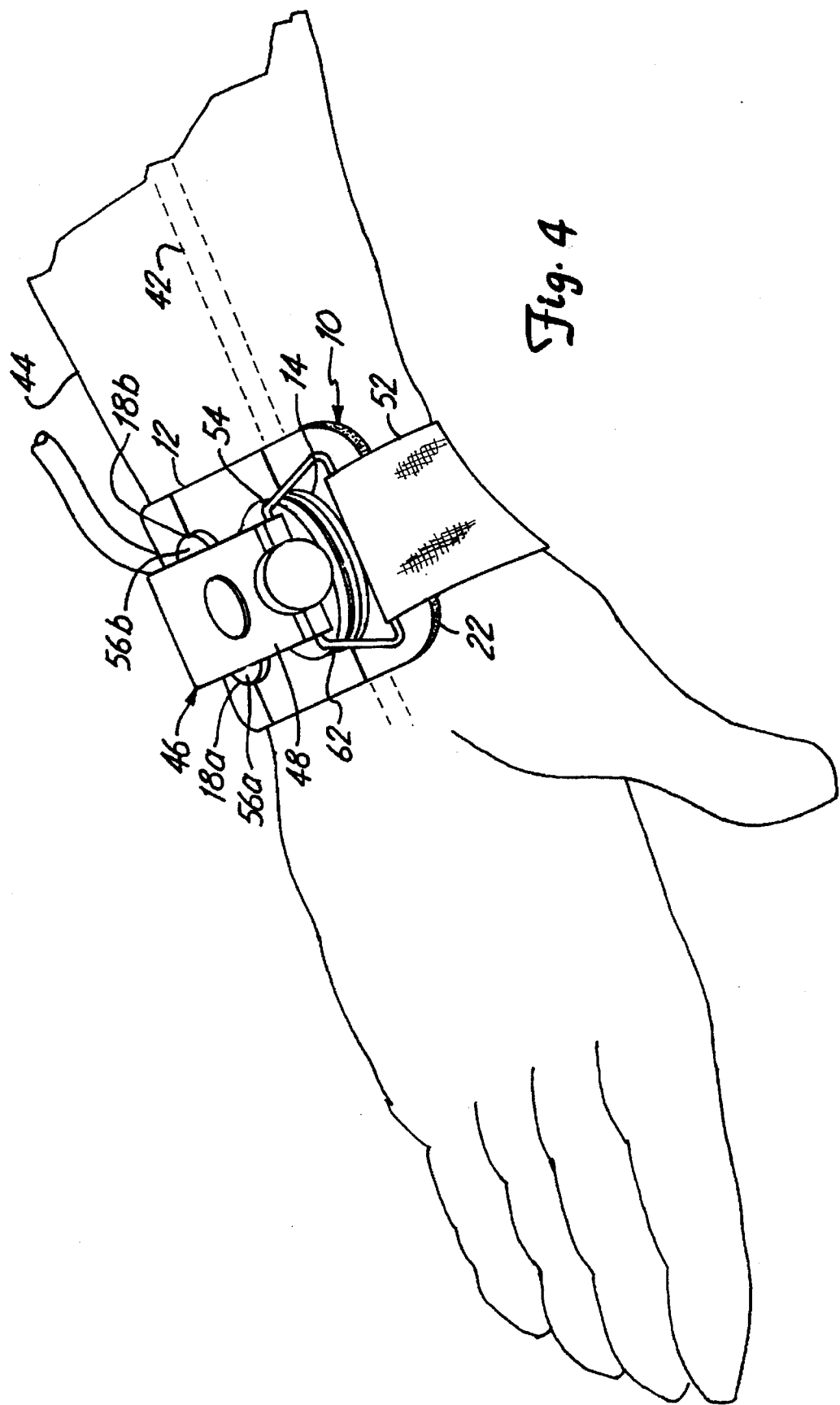
FIG. 4 is a perspective view of the sensor locator locating the blood pressure sensing device over an underlying artery.

FIG. 4 is a perspective view illustrating sensing device 46 wrapped about wrist 44 and accurately centered over artery 42 by sensor locator 10. As best shown by FIG. 4, window 14 receives sensor interface 54 to guide and center sensor interface 54 over artery 42. At the same time, windows 18a, 18b receive wrist pads 56a, 56b, respectively, to further ensure accurate placement of sensing device 46 with respect to wrist 44 and artery 42. In addition to guiding the placement and location of sensing device 46, sensor locator 10 also stabilizes sensing device 46 to prevent accidental movement of sensing device 46 out of an aligned relationship with artery 42. Because window 14 and windows 18a, 18b have shapes at least partially corresponding to the shapes of sensor interface 54 and wrist pads 56a, 56b, respectively, base 12 mates with sensor interface 54 and wrist pads 56a, 56b. Because window 14 and windows 18 preferably have shapes identically corresponding to the shapes of sensor interface 54 and wrist pads 56 and because windows 14 and windows 18 are encircled or completely defined by base 12, base 12 abuts and engages all points about the perimeter of sensor interface 54 and wrist pads 56 of sensing device 46. As a result, locator 10 stabilizes sensing device 46 against accidental movement in virtually any lateral or transverse direction relative to wrist 44. Furthermore, because base 12 has a non-deminimus thickness, preferably 3/32 of an inch, the surface area of base 12 abutting and engaging sensor interface 54 and wrist pads 56a, 56b is substantial to stabilize sensing device 46 against accidental movement.

Although illustrated as being for use with sensing device 46, sensor locator 10 may alternatively be used with a wide variety of non-invasive, external blood pressure sensors. As can be appreciated, the size, shape and location of windows 14 and 18a, 18b may be modified based upon a corresponding size, shape and location of the sensor interface and contact points of the alternative sensing device. Furthermore, the number of windows as well as the shape of windows may be modified independent of the alternative sensing device. For example, windows 18 may be omitted or additional windows may be added to sensor locator 10. Furthermore, the shape of windows 14 and 18a, 18b may constitute any of a variety of shapes such as rectangular, triangular, octagonal or semi-circular depending upon corresponding shapes of sensing device 46. In addition, windows 14 and 18a, 18b may alternatively comprise openings such as notches which are formed in side edges of base 12 and which are configured for at least partially receiving and at least partially mating with corresponding surfaces of a sensing device.

In conclusion, the sensor locator of the present invention accurately and precisely locates a blood pressure sensing device over an underlying artery. Once a sensor locator is in place, the exact location at which the sensing device must be positioned is marked and identified until the sensor locator is removed. Consequently, sensor locator 10 enables a physician to quickly and accurately mount the sensing device over the underlying artery a multitude of times during different stages of a patient's treatment. Because the sensor locator of the present invention is preferably adhesively secured to the anatomy of the patient, the sensor locator does not circumvent the anatomy such as the wrist. As a result, swelling and other undesirable results caused by the occlusion or reduction of blood flow are prevented. In addition to enabling accurate and precise repeated positioning of a sensing device over an underlying artery, sensor locator 10 also stabilizes a sensing device against accidental movement or dislodgement brought about by patient movement. Because sensor locator 10 is preferably formed from lightweight, breathable and flexible material, sensor locator 10 is lightweight and easily wraps about varying anatomies. Consequently, sensor locator 10 is comfortable and less fatiguing to the patient. Overall, the sensor locating device of the present invention enables a physician to more accurately and efficiently measure blood pressure of a patient's artery.

Although the present invention has been described with reference to preferred embodiments, workers skilled in the art will recognize that changes may be made in form and detail without departing from the spirit and scope of the invention.

What is claimed is:

1. A blood pressure sensor locator for locating a blood pressure sensing device over an underlying artery of a patient, the locator being separate from the sensing device, the locator comprising:

a flexible base;

means for coupling the flexible base in a selected position adjacent an anatomy of the patient proximate the underlying artery; and a guide opening through the flexible base and configured to locate and align the sensing device over the underlying artery when the sensing device is connected to the patient; so that the sensing device can be attached to and removed from the patient without disturbing the position of the flexible base.

2. The locator of claim 1 wherein the base is flexible so as to conform to the anatomy of the patient.

3. The locator of claim 1 wherein the flexible base includes a layer of open celled foam.

4. The locator of claim 1 wherein the guide opening is sized for at least partially mating with and at least partially receiving the sensing device.

5. The locator of claim 4 wherein the locator includes a transparent thin film spanning the guide opening.

6. The locator of claim 5 wherein the thin film includes alignment marks for aligning the guide opening over the underlying artery.

7. The locator of claim 4 wherein the guide opening is surrounded by the base and is sized for receiving a portion of the sensing device and wherein the base engages the portion of the sensing device about the guide opening to maintain the sensing device over the underlying artery.

8. The locator of claim 1 wherein the flexible base includes at least one additional opening spaced from the guide opening and sized for at least partially mating with and at least partially receiving a portion of the sensing device.

9. The locator of claim 1 wherein edges of the flexible base defining the guide opening engage the sensing device on opposite peripheries of the sensing device.

10. The locator of claim 1 wherein the guide includes at least one alignment mark for alignment with the underlying artery.

11. The locator of claim 1 wherein the guide includes aligning means for aligning the sensing device with the locator.

12. The locator of claim 1 wherein the means for coupling includes:

an adhesive on an underside of the flexible base for coupling the flexible base to an anatomy of the patient.

13. A blood pressure sensor locator for defining where a separate blood pressure sensing device should be positioned over an underlying artery of a patient, the locator comprising:

a flexible template including at least one surface shaped for mating with a corresponding shaped surface of the sensing device to align the sensing device with the flexible template; and means for coupling the flexible template in a selected position proximate the underlying artery so that the sensing device can be separately attached to and detached from the patient without disturbing the position of the flexible template.

14. The locator of claim 13 wherein the flexible template includes at least one opening through the flexible template, wherein said at least one surface defines a perimeter of the opening.

15. The locator of claim 14 wherein the sensing device includes a sensing member for being positioned over the underlying artery and wherein said at least one opening receives the sensing member.

16. The locator of claim 13 wherein the sensing device includes a support surface for supporting the sensing device adjacent an anatomy of the patient and wherein the flexible template includes an opening sized for receiving the supporting surface.

17. The locator of claim 14 wherein the locator further includes a transparent thin film across the opening.

18. The locator of claim 17 wherein the transparent thin film includes at least one alignment mark for aligning the opening over the underlying artery.

19. The locator of claim 18 wherein the alignment mark comprises a pair of cross hairs.

20. The locator of claim 13 wherein the flexible template includes at least one alignment mark for aligning the template with the underlying artery.

21. The locator of claim 13 wherein the flexible template includes:

means for aligning the sensing device with the flexible template.

22. The locator of claim 21 wherein the means for aligning includes:

a plurality of spaced windows sized for receiving spaced portions of the sensing device.

23. A blood pressure sensor locating template for locating a sensing surface of a blood pressure sensing device over an underlying artery, the sensing device being separable from the locating template and being capable of attachment to a patient, the locating template comprising:

a flexible base having a first opening extending through the base, wherein the first opening is configured for receiving the sensing surface of the sensing device so that the flexible base at least partially mates with a first portion of the sensing device about the first opening;

at least one alignment indicator for aligning the flexible base relative to the underlying artery; and means for coupling the flexible base to the patient independent of the sensing device so that the sensing device can be separately attached to and detached from the patient without disturbing positioning of the flexible base.

24. The locating template of claim 23 wherein the flexible base includes a second opening extending through the flexible base and wherein the second opening is spaced from the first opening and is configured for at least partially receiving a second portion of the sensing device so that the base at least partially mates simultaneously with the first and second portions of the sensing device.

25. A method for locating a blood pressure sensor over an underlying artery of a patient, the method comprising:

identifying a location on the patient above the underlying artery;

attaching a flexible sensor locator to the patient adjacent the identified location in a preselected aligned relationship with the location;

positioning the blood pressure sensor over the underlying artery in a preselected aligned relationship with the locator; and attaching the blood pressure sensor to the patient without attachment to the flexible sensor locator so that the blood pressure sensor can be removed without disturbing positioning of the flexible sensor locator.

* * * * *

UNITED STATES PATENT AND TRADEMARK OFFICE
CERTIFICATE OF CORRECTION

PATENT NO. : 5,642,733
DATED : JULY 1, 1997
INVENTOR(S) :
G. KENT ARCHIBALD, ORLAND H. DANIELSON, ROGER J. WOESSNER

It is certified that error appears in the above-indentified patent and that said Letters Patent is hereby corrected as shown below:

Col. 7, line 45, delete claim 2, "The locator of claim 1 wherein the based is flexible so as to conform to the anatomy of the patient."

Signed and Sealed this

Second Day of December, 1997

*Attest:*

BRUCE LEHMAN

*Attesting Officer*  *Commissioner of Patents and Trademarks*